US008852628B1

(12) United States Patent
Houze et al.

(10) Patent No.: US 8,852,628 B1
(45) Date of Patent: Oct. 7, 2014

(54) TRANSDERMAL DRUG DELIVERY SYSTEM FOR DICLOFENAC

(75) Inventors: David Houze, Miami, FL (US); Samara Hantman, Miami, FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 0 days.

(21) Appl. No.: 13/616,919

(22) Filed: Sep. 14, 2012

Related U.S. Application Data

(63) Continuation of application No. 12/804,009, filed on Jul. 12, 2010, now abandoned.

(60) Provisional application No. 61/270,749, filed on Jul. 13, 2009.

(51) Int. Cl.
*A61K 9/70* (2006.01)
*A61K 9/00* (2006.01)

(52) U.S. Cl.
CPC ................................. *A61K 9/0014* (2013.01)
USPC ......................................... 424/448; 424/449

(58) Field of Classification Search
None
See application file for complete search history.

(56) References Cited

U.S. PATENT DOCUMENTS

| | | | |
|---|---|---|---|
| 6,951,598 B2 * | 10/2005 | Flugge et al. | 162/164.4 |
| 2004/0033254 A1 * | 2/2004 | Song et al. | 424/449 |
| 2005/0215643 A1 * | 9/2005 | Reiner et al. | 514/567 |
| 2008/0220068 A1 | 9/2008 | Masini-Eteve et al. | |

OTHER PUBLICATIONS

Office Action issued on Jan. 10, 2012 by the Examiner in U.S. Appl. No. 12/804,009.
Office Action issued on Mar. 16, 2012 by the Examiner in U.S. Appl. No. 12/804,009.
Song et al., "Overview of factors affecting oral drug absorption," Asian Journal of Drug Metabolism and Pharmacokinetics, vol. 4, No. 3, pp. 167-176, 2004.
Huang et al., "Mechanistic Approaches to Predicting Oral Drug Absorption," The AAPS Journal, vol. 11, No. 2, pp. 217-224, Jun. 2009.
Barry, "Breaching the skin's barrier to drugs," Nature Biotechnology, vol. 22, No. 2, pp. 165-167, Feb. 2004.
Sadrieh, "Challenges in the Development of Transdermal Drug Delivery Systems," U.S. Food and Drug Administration, Advisory Committee for Pharmaceutical Science and Clinical Pharmacology, Aug. 5, 2009.
Block, "Medicated Topicals," Remington: The Science and Practice of Pharmacy, $20^{th}$ ed., Chapter 44, pp. 836-857, 2006.
Hughes et al., "Appropriate use of transdermal drug delivery systems," Journal of Nursing Education and Practice, vol. 3, No. 10, pp. 129-138, 2013.
Federal Drug Administration, "Summary of NDA Approvals and Receipts—1938 to present," http:www.fda.gov/AboutFDA/WhatWeDo/History/ProductRegulation/SummaryofNDA, accessed on Dec. 2, 2013.

* cited by examiner

*Primary Examiner* — Peter J Reddig
*Assistant Examiner* — Sarah Chickos
(74) *Attorney, Agent, or Firm* — Foley & Lardner LLP

(57) ABSTRACT

Disclosed is a transdermal composition for delivery of diclofenac comprising the use of a pharmaceutically acceptable acid or salt form in an admixture with a pharmaceutically acceptable adhesive matrix carrier. In a preferred embodiment, diclofenac is present as the free acid and potassium salt form in the adhesive matrix composition together with a dual permeation enhancer. The adhesive matrix composition is applied in a method of substantially increasing drug delivery for 24 or more hours.

15 Claims, 2 Drawing Sheets

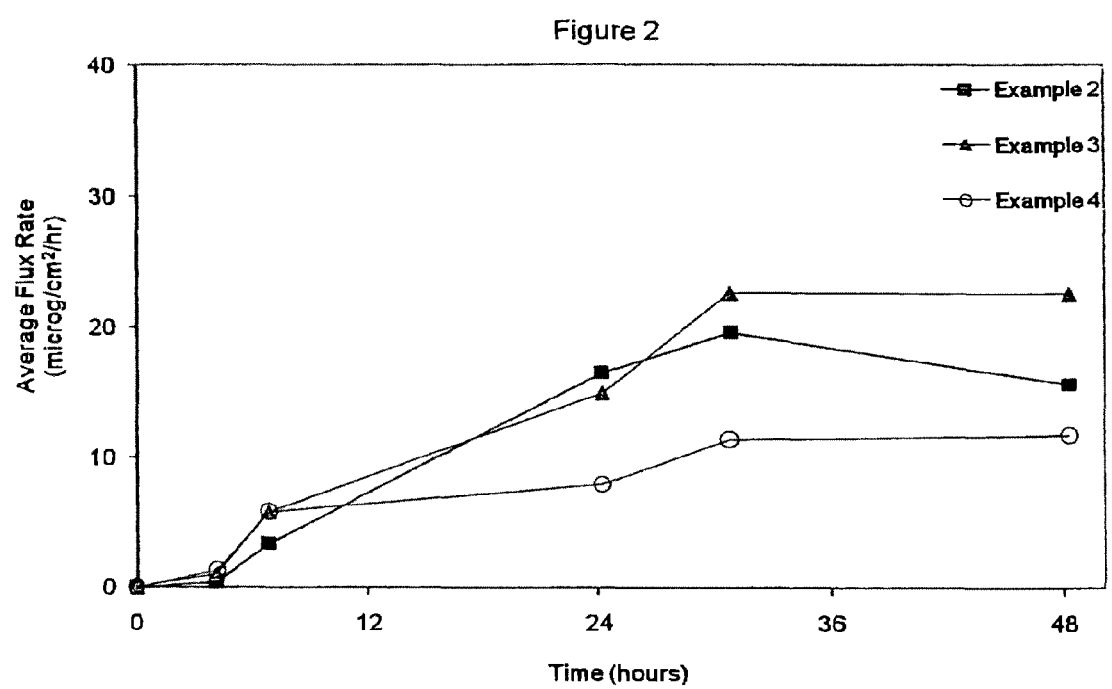

TRANSDERMAL DRUG DELIVERY SYSTEM FOR DICLOFENAC

SCOPE OF THE INVENTION

The present invention is directed to a transdermal delivery system for diclofenac. This delivery system is a drug-containing adhesive system which has an improved delivery rate over a period of time.

BACKGROUND OF THE INVENTION

Diclofenac, 2-(2,6-dichloro-anilino)-phenyl-acetic acid, is known as a non-steroidal anti-inflammatory drug (NSAID). NSAIDs produce their therapeutic activities through inhibition of cyclooxygenase (COX), the enzyme that makes prostaglandins (PGs). COX-1 makes PGs that protect the stomach and kidneys. COX-2 produces PGs that cause pain and inflammation. Diclofenac is a non-selective NSAID that inhibits both types of COX enzymes1.

The analgesic properties of diclofenac make it effective in cases of moderate to severe pain where rapid relief is required. Diclofenac is used to treat a wide range of musculoskeletal disorders, including muscular aches, sprains, strains, tendonitis (tendon inflammation), bursitis, bruises, fractures and dislocations. It is effective in the treatment of joint disorders, including arthritis, osteoarthritis (a degenerative joint condition), rheumatoid arthritis (inflammation of the joints), ankylosing spondylitis (an inflammation of the vertebrae), and pyrophosphate arthropathy (crystal deposits in the joints).

Diclofenac is also used to provide relief for those who suffer from acute gout, lower back pain, migraine headache, menstrual pain and dysmenorrhoea. It can alleviate the discomfort associated with inflammatory infections of the ear, nose, or throat, post-operative pain or inflammation due to trauma following dental, orthopaedic, or other minor surgery.

Diclofenac is available in solid dose formulations. The commercially available oral pharmaceuticals are formulated for rapid-acting effect. However, it is recommended to avoid taking them on an empty stomach as they have side effects such as stomach discomfort. When they are taken after eating, the initial absorption of diclofenac is outstandingly reduced in the amount and delayed in the rate compared with the case where they are taken on an empty stomach, and in some cases, the maximum absorption is confirmed at several hours to ten and several hours after taking them, and also individual difference is large in the absorption thereof. Rectal suppositories provide a more reliable rapid-acting effect, but there are many patients who are reluctant to use the suppositories.

Diclofenac is also available in topical formulations such as gels and patches. Gels require special handling and care, and can be less convenient to use as they interact with clothing and water. The commercially available patch is comprised of an adhesive material containing 180 mg of diclofenac epolamine in an aqueous base and measures 10 cm×14 cm (about 4 inches by 5.5 inches). The recommended dose is to apply one patch to the most painful area twice a day.

Consequently, today there is a strong request for diclofenac in forms providing convenience, fast effect and delivery certainty. The objective is to develop a daily, and more preferably a multi-day, single-dose transdermal delivery device.

SUMMARY OF THE INVENTION

The present invention is directed to a transdermal delivery system for an active substance. The active substance is diclofenac and/or its derivatives, and preferably one or more of its alkali and organic salts and its free acid. The system comprises a backing layer, preferably moisture permeable, and an adhesive matrix affixed thereto, and a release liner. The total adhesive matrix composition comprises, on a dry weight percentage from about 5% to about 20% of a matrix constituent, from about 5% to about 25% of one or more permeation enhancers, and from about 10% to about 40% of the active substance.

DESCRIPTION OF THE DRAWINGS

FIG. 2 is a graph illustrating the drug flux from compositions containing diclofenac potassium and acid with two differing concentrations of diclofenac potassium, and a composition containing only diclofenac potassium.

DETAILED DESCRIPTION OF THE INVENTION

Figure 1:
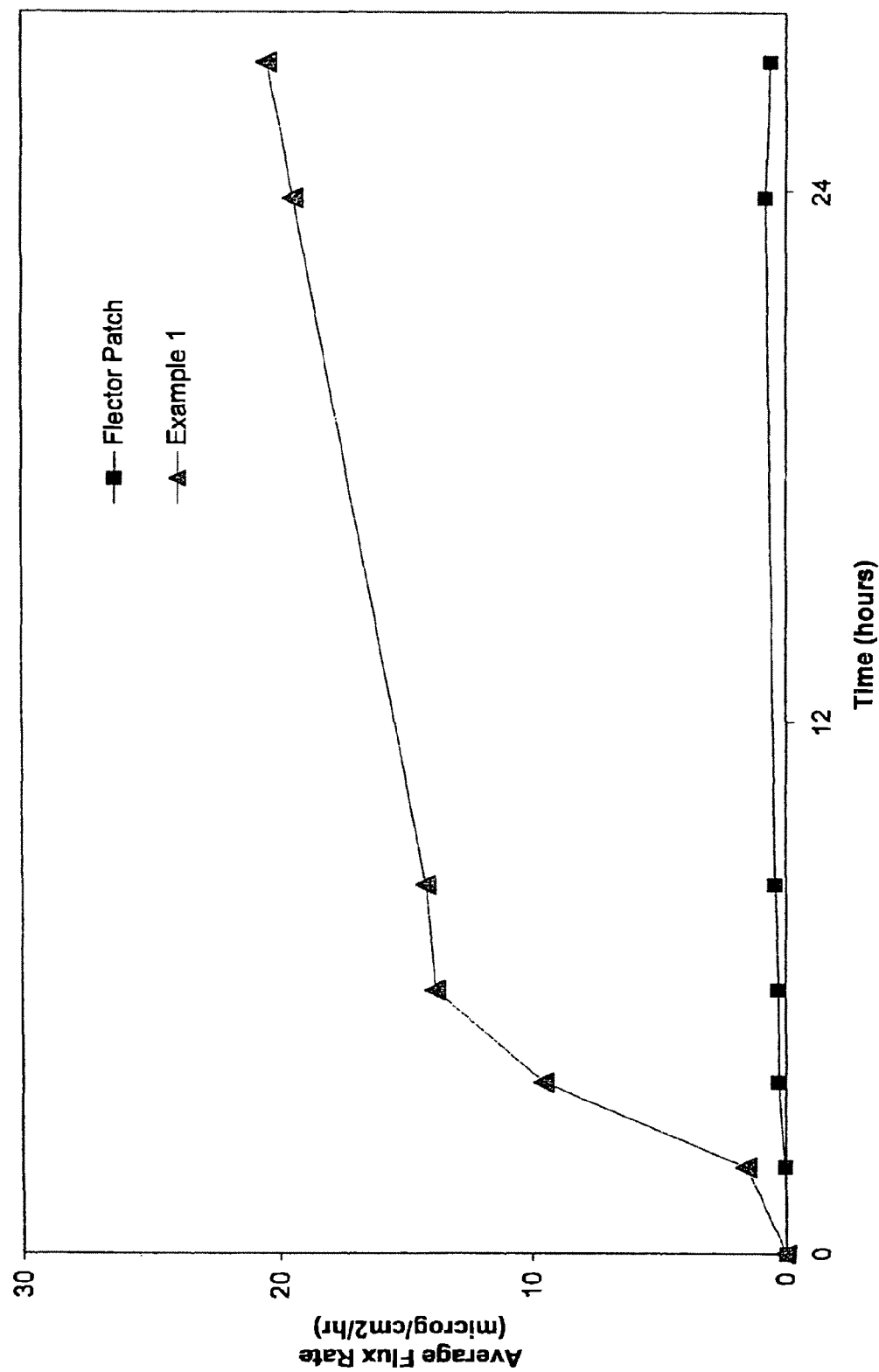
FIG. 1 is a graph illustrating the drug flux of diclofenac from a composition containing diclofenac potassium and acid and the flux of diclofenac from a transdermal drug delivery system called FLECTOR® sold by King Pharmaceuticals, Inc.

It is the object of the present invention to provide a pharmaceutical composition for transdermal application containing diclofenac or one or more pharmaceutically acceptable salts thereof, which composition is distinguished by enhanced permeation properties.

The present invention also relates to a drug-in-adhesive system that is preferably formulated so that it is a pressure-sensitive adhesive at room temperature and has other desirable characteristics for adhesives used in the transdermal drug delivery art, such as good adherence to skin and cohesivity to accommodate higher drug concentrations, while delivering a therapeutically effect amount of drug for 24 hours or more.

The invention further relates to a method for increasing drug loading in order to achieve a drug delivery profile capable of delivering beyond 24 hours for potentially a multi-day product by enhancing the permeability of diclofenac as a pharmaceutically acceptable salt thereof in transdermal formulations.

The diclofenac that can be used in this method includes, but is not limited to, a free acid of diclofenac, an alkali metal salt such as the sodium or potassium salt, or an organic salt, especially an amine salt, such as, for example, diethylamine. A particularly preferred embodiment includes a combination of diclofenac acid and diclofenac potassium. It has further been found that the potassium salt drug form more readily blends in suitable solvent-based adhesives used in adhesive matrix type carriers.

In addition, for increasing the concentration of the active ingredient within the matrix, a solubility enhancer may also be employed in the invention, for example polyvinylpyrrolidone polymers, polyethylene oxide, polyacrylic acid, polyvinyl alcohol, silicone dioxide, silica, celluloses and cellulose derivatives such as hydroxymethyl cellulose, hydroxypropyl cellulose, gelatins, gums, starches, dextrins and dextrans, sterols, bile acids and other similar agents. A preferred embodiment of the invention uses soluble polyvinylpyrrolidone (PVP) as a matrix constituent. As such, the matrix layer can be thin with high concentrations of the active ingredient within the patch. Soluble PVP is preferably present composition in an amount ranging from about 5% to about 20% and more preferably from about 10% to about 20% by weight of the total adhesive matrix composition.

The term "polyvinylpyrrolidone," or "PVP" refers to a polymer, either a homopolymer or copolymer, containing N-vinylpyrrolidone as the monomeric unit. Typical PVP polymers are homopolymeric PVPs and the copolymer vinyl acetate vinylpyrrolidone. The homopolymeric PVPs are known to the pharmaceutical industry under a variety of designations including Povidone, Polyvidone, Polyvidonum, Polyvidonum solubile, and Poly(1-vinyl-2-pyrrolidone). The copolymer vinyl acetate vinylpyrrolidone is known to the pharmaceutical industry as Copolyvidon, Copolyvidone, and Copolyvidonum.

The term "soluble" when used with reference to PVP means that the polymer is soluble in water and generally is not substantially cross-linked, and has a molecular weight of less than about 2,000,000. The PVP usable with the present invention preferably has a high molecular weight of from about 500,000 to about 1,500,000, and more preferably about 1,100,000. See, generally, Buhler, KOLLIDON®: POLYVINYLPYRROLIDONE FOR THE PHARMACEUTICAL INDUSTRY, BASF Aktiengesellschaft (1992). "KOLLIDON®" is a trademark of BASF AG, Ludwigshafen, Germany, for a polyvinylpyrrolidone (PVP) polymer. Preferred are "KOLLIDON® 30 and 90."

Suitable permeation enhancers to facilitate transdermal transport of drug into and/or throughout the skin are described are described in U.S. Pat. No. 6,221,383. They can include polyhydric alcohols such as dipropylene glycol, propylene glycol, and polyethylene glycol; fatty ethers such as cetyl ether and oleyl ether; fatty acid esters such as isopropyl myristate; aliphatic surfactants such as methyl and lauryl sulfates; aliphatic alcohols; polyoxyethylene ethers; oleic and linoleic acids; propyl oleate; and isopropyl palmitate. Particularly preferred are combinations of one or more polyhydric alcohols such as glycerine, dipropylene glycol, butylene glycol, propylene glycol and oleyl alcohol and oleic acid. In a particularly preferred embodiment, the permeation of diclofenac is enhanced by a combination of dipropylene glycol and oleic acid, wherein the total amount of dipropylene glycol ranges from about 30% to about 40% of the amount of oleic acid based on the total dry weight of the entire drug-containing adhesive matrix composition.

The drug-containing adhesive matrix composition is a pressure-sensitive adhesive and is acceptable for medical use. Of the types of suitable polymers for the matrix, preferably included are at least one acrylic-based polymer and one rubber. In a particularly preferred embodiment, a non-functional acrylic-based polymer is used with an amine-compatible polysiloxane.

The term "acrylic-based" polymer is defined as any polyacrylate, polyacrylic, acrylate and acrylic polymer. The acrylic-based polymers can be any of the copolymers, terpolymers, and the like of various acrylic acids or esters. The acrylic-based polymers useful in practicing the invention are polymers of one or more monomers of acrylic acids and other copolymerizable monomers. The acrylic-based polymers also can include copolymers of alkyl acrylates and/or methacrylates and/or copolymerizable secondary monomers. The acrylic-based polymer may be functional or non-functional. As used herein "non-functional" means an acrylic-based polymer that has no or substantially no functional reactive moieties present in the acrylic. These are generally acrylic esters, alkyl acrylates or methacrylates which can be copolymerized with other monomers which do not have functional groups. As used herein, "functional monomers or groups," are monomer units in acrylic-based polymers which have reactive chemical groups which modify the acrylic-based polymers directly or provide sites for further reactions. Examples of functional groups include carboxyl, epoxy and hydroxy groups.

Suitable acrylic-based polymers that are also pressure-sensitive adhesives are commercially available and include the acrylic-based adhesives sold under the trademarks DURO-TAK® by Henkel, Bridgewater, N.J. (such as 87-2287, -2296, -2510, -2852, -4852, -9085, -9088 and 900A). Other suitable acrylic-based adhesives include those sold under the trademark EUDRAGIT® by Roehm Pharma GmbH, Darmstadt, Germany; those sold by Cytec Surface Specialties; St. Louis, Mo., under the trademarks GELVA® Multipolymer Solution (such as 1151, 1753, 2495, 2999, 3087, 3235, 9067, 9073 and 9083).

The term "rubber" refers to a viscoelastic material which has the properties of a pressure-sensitive adhesive and which contains at least one natural or synthetic elastomeric polymer. Suitable rubbers include silicone-based polymers such as polysiloxane, polyisobutylene and natural rubber, with polysiloxane being preferred.

The term "silicone-based" polymer is intended to be used interchangeably with the terms siloxane, polysiloxane, and silicones as used herein and as known in the art. The silicone-based polymer may also be a pressure-sensitive adhesive, with a polysiloxane adhesive prepared by cross-linking an elastomer, typically a high molecular weight polydiorganosiloxane, with a resin, to produce a three-dimensional siloxane structure, via a condensation reaction in an appropriate organic solvent. Suitable silicone pressure-sensitive adhesives are commercially available and include those sold under the trademarks BIO-PSA® by Dow Corning Corporation, Medical Products, Midland, Mich. such as 7-4102, -4201, -4202, -4302, -4402, -4502, and -4603, with those designated as amine compatible being preferred for use with higher drug concentrations, such as those in preferred embodiments, to increase matrix cohesion.

The adhesive coated release liner is then dried and laminated onto a backing using known methods. The backing can be occlusive, non-occlusive or a breathable film as desired, breathable backings being particularly preferred. In practice of the preferred embodiments of the invention, use of backing layers or films that are occlusive to moisture and therefore do not permit moisture to be transmitted out of the patch are less effective in maintaining cohesiveness of the adhesive matrix and in achieving desired sustained drug delivery. Further details and examples of breathable backings which are useful in the practice of this invention are well known in the art, such as those described in Sablotsky et al., U.S. Pat. No. 4,994,278. The backing is flexible such that it conforms to the skin. It can be any of the commonly used materials for backing layers in transdermal systems including polyethylene, polyester, polypropylene, ethylene-vinyl acetate copolymers, polyurethane, and the like. Backings that are layered, co-extruded or laminated are also suitable. The backing should be substantially non-reactive with the ingredients of the formulation.

A transdermal drug delivery system in accordance with this invention containing pharmaceutically acceptable diclofenac salts can be used to treat any condition capable of treatment with this drug and in particular the treatment of inflammation and the relief of pain. The device can be placed on the skin and allowed to remain for a time sufficient to achieve or maintain the intended therapeutic effect. The time that constitutes a sufficient time can be selected by those skilled in the art with consideration of the delivery rate of the transdermal system of this invention and upon the condition being treated.

An exemplary general method for the preparation of an embodiment is as follows: 1. Appropriate amounts of solvent(s), co-solvent(s), enhancer(s), matrix constituents, and non-aqueous volatile processing solvent(s) (for example, toluene, ethyl acetate, isopropyl alcohol, etc.) are combined and thoroughly mixed together in a vessel. 2. The drug(s) are then added to the mixture and agitation is carried out until the drug is uniformly mixed in. 3. Appropriate amounts of polymer(s) are then added to mixture, and thoroughly mixed. 4. The formulation is then transferred to a coating operation where it is coated onto a protective release liner at a controlled specified thickness. The coated product is then passed through an oven in order to drive off all volatile processing solvents. 5. The dried product on the release liner is then joined to the backing material and wound into rolls for storage. 6. Appropriate size and shape "systems" are die-cut from the roll material and then pouched.

The order of steps, the amount of the ingredients, and the amount and time of agitation or mixing may be importance process variables which will depend on the specific polymers, drugs, solvents, and enhancers used in the formulation. These factors can be adjusted by those skilled in the art, while keeping in mind the object of providing a uniform product. It is believed that a number of other methods, including changing some of the order of steps, can be carried out and will give desirable results.

EXAMPLES

The above description and following specific examples are hereby illustrative of pharmaceutically acceptable active agent carrier compositions and transdermal drug delivery systems, and methods of making same, within the contemplation of the invention. The description and examples are in no way intended to be, or should be considered, limiting of the scope of the invention. And while efforts have been made to ensure accuracy with respect to numbers used (such as amounts and temperatures), some experimental error and deviation should be accounted for and/or allowed. The weights percentages in the examples are based on dry weight of the total adhesive matrix system, unless other noted.

The following commercially available polymers were used in the examples:

"DURO-TAK® 87-4852" is a trademark of HENKEL (National Adhesives), Bridgewater, N.J. for polyacrylate adhesives in organic solutions.

"BIO-PSA® 7-4202" is a trademark of DOW CORNING CORPORATION, MEDICAL PRODUCTS, Midland, Mich. for polysiloxane adhesives in organic solutions.

"KOLLIDON® 90" is a trademark of BASF Aktiengesellschaft, Ludwigschaften, Germany for polyvinylpyrrolidone polymers.

PLASDONE® K-90 (Povidone U.S.P) is a trademark of GAF Corporation.

The flux data was collected from an in-vitro permeation study utilizing modified Franz cells with stratum corneum obtained from human cadaver skin by the heat separation technique. The receiver solution for this study was 0.9% NaCl with 0.01% NaN3 in deionized water. Franz cells were maintained at about 32° C. for the duration of this study. Flux samples were analyzed by HPLC.

Transdermal delivery compositions were prepared with the following ingredients:

TABLE 1

| Components | Examples 1 & 3 | Example 2 | Example 4 |
|---|---|---|---|
| BIO-PSA ® 7-4202 | 33 | 47 | 41 |
| DURO-TAK ® 87-4852 | 5 | 5 | 5 |
| Oleic Acid | 12 | 12 | 12 |
| Dipropylene Glycol | 4 | 4 | 4 |
| PLASDONE ® K-90 | 16 | 16 | 16 |
| Diclofenac Potassium | 16 | 16 | 8 |
| Diclofenac Acid | 14 | 0 | 14 |

When diclofenac sodium, acid and potassium were fluxed as single entities in formulations similar to those described in the examples, diclofenac potassium was found to flux at the highest rate, particularly when combined with oleic acid and dipropylene glycol, but lower than with formulations incorporating additional diclofenac salts. When the potassium salt is combined with diclofenac acid, the flux rate achievable is capable for delivering in excess of 24 hours as seen from Example 3 in FIG. 2. Decreasing the potassium salt concentration by 50% seems to decrease the flux by about 50% as seen from Example 4. Moreover, as seen from FIG. 1, the average flux rate is approximately 27 times higher as compared to the commercially available Elector Patch. Accordingly, in order to deliver within a therapeutic effective range of about 7 mg to about 15 mg diclofenac per day, a transdermal patch of this invention could be produced in the range of about 25 cm to about 40 cm squared.

What is claimed is:

1. A transdermal delivery composition comprising:
an adhesive matrix composition comprising on a dry weight percentage basis from about 30% to about 95% of one or more polymers,
from about 5% to about 20% of a solubility enhancer,
from about 5% to about 25% of a permeation enhancer, and
from about 10% to about 40% of diclofenac,
wherein the diclofenac is provided as a combination of diclofenac acid and a pharmaceutically acceptable salt of diclofenac.

2. The composition according to claim 1, wherein the diclofenac is a combination of diclofenac acid and diclofenac potassium.

3. The composition according to claim 1, wherein the permeation enhancer is one or more polyhydric alcohols.

4. The composition according to claim 3, wherein the permeation enhancer is dipropylene glycol and oleic acid, and the dipropylene glycol is present in an amount of about 30% to about 40% of the amount of the oleic acid based on the total dry weight of the adhesive matrix composition.

5. The composition according to claim 1, wherein the one or more polymers are selected from the group consisting of acrylic-based polymers and rubbers and combinations thereof.

6. The composition according to claim 5, wherein the acrylic-based polymer is a non-functional acrylic polymer and the rubber polymer is a polysiloxane.

7. The composition according to claim 6, wherein polysiloxane is amine-compatible.

8. The composition according to claim 1, further comprising a backing layer that is not occlusive to moisture.

9. A transdermal delivery composition comprising:
an adhesive matrix composition comprising on a dry weight percentage basis from about 30% to about 95% of one or more polymers selected from the group consisting of non-functional acrylic-based polymers and polysiloxanes, from about 5% to about 20% of a soluble polyvinylpyrrolidone, from about 5% to about 25% of a combination of dipropylene glycol and oleic acid, wherein the dipropylene glycol is present in an amount of about 30% to about 40% of the amount of the oleic acid based on the total dry weight of the adhesive matrix composition and from about 10% to about 40% of diclofenac, wherein the diclofenac is provided as a combination of diclofenac acid a pharmaceutically acceptable salt of diclofenac.

10. The composition according to claim 9, wherein the pharmaceutically acceptable salt of diclofenac is diclofenac potassium.

11. The composition according to claim 10, wherein the polysiloxane is amine-compatible.

12. The composition according to claim 11, wherein the adhesive matrix composition is capable of delivering a therapeutic effective range of about 7 mg to about 15 mg diclofenac per day.

13. The composition according to claim 11, wherein the adhesive matrix composition is capable of transdermally delivering about 7 mg to about 15 mg diclofenac over a period of time in excess of 24 hours.

14. A method of enhancing the transdermal delivery of diclofenac from a transdermal delivery composition, comprising administering to a subject in need thereof the transdermal delivery composition of claim 1, wherein the diclofenac is provided as a combination of diclofenac acid and a pharmaceutically acceptable salt of diclofenac in an amount sufficient to deliver a therapeutically effective amount of diclofenac for 24 hours or more.

15. The method of claim 14, wherein the transdermal composition comprises an adhesive matrix composition comprising on a dry weight percentage basis from about 30% to about 95% of one or more polymers selected from the group consisting of non-functional acrylic-based polymers and polysiloxanes, from about 5% to about 20% of a soluble polyvinylpyrrolidone, from about 5% to about 25% of a combination of dipropylene glycol and oleic acid, wherein the dipropylene glycol is present in an amount of about 30% to about 40% of the amount of the oleic acid based on the total dry weight of the adhesive matrix composition, and from about 10% to about 40% of diclofenac, wherein the diclofenac is provided as a combination of diclofenac acid and a pharmaceutically acceptable salt of diclofenac.

* * * * *